(12) United States Patent
Villalobos

(10) Patent No.: US 7,977,378 B1
(45) Date of Patent: Jul. 12, 2011

(54) COMPOSITIONS AND METHODS FOR ENHANCING WEIGHT-LOSS BY CYCLICAL ADMINISTRATION OF COMPOUNDS

(76) Inventor: Adel Villalobos, Mission Hills, CA (US)

( * ) Notice: Subject to any disclaimer, the term of this patent is extended or adjusted under 35 U.S.C. 154(b) by 484 days.

(21) Appl. No.: 11/960,696

(22) Filed: Dec. 19, 2007

(51) Int. Cl.
| | |
|---|---|
| *A61K 31/353* | (2006.01) |
| *A61K 31/137* | (2006.01) |
| *A61K 31/216* | (2006.01) |
| *A61K 31/235* | (2006.01) |
| *A61K 31/522* | (2006.01) |
| *C07D 463/14* | (2006.01) |
| *C07D 487/14* | (2006.01) |
| *C07D 487/22* | (2006.01) |
| *C07D 471/14* | (2006.01) |
| *C07D 473/12* | (2006.01) |
| *C07D 311/32* | (2006.01) |
| *C07D 311/62* | (2006.01) |
| *C07C 215/08* | (2006.01) |
| *C07C 215/30* | (2006.01) |

(52) U.S. Cl. ........ 514/456; 514/257; 514/653; 514/513; 514/263.34; 549/406; 544/245; 544/273; 564/365; 560/183

(58) Field of Classification Search .................. None
See application file for complete search history.

(56) References Cited

U.S. PATENT DOCUMENTS

| | | | | |
|---|---|---|---|---|
| 5,716,976 | A * | 2/1998 | Bernstein | 514/386 |
| 2006/0229274 | A1 * | 10/2006 | Hsue | 514/47 |
| 2009/0054372 | A1 * | 2/2009 | Goldsmith | 514/52 |

OTHER PUBLICATIONS

Richard B. Silverman, "The Organic Chemistry of Drug Design and Drug Action" published 1992 by Academic Press, chapter 2, pp. 4-47.*

"STN Database Descriptions" 2006 Chemical Abstracts catalog, published 2006 by Chemical Abstracts Service, p. 52.*

* cited by examiner

*Primary Examiner* — Eric S Olson
(74) *Attorney, Agent, or Firm* — Nancy Lord, Ltd.; Nancy Lord

(57) ABSTRACT

Compositions and methods are provided for the treatment of obesity in a human in need of such treatment which comprises administration to the human of a therapeutically effective amount of a compound of a weight loss enhancing beta-3-adrenergic compound of Cycle I, and a different weight loss enhancing adenylate cyclase receptor replenishing compound of Cycle II, in conjunction with a pharmaceutically acceptable diluent or carrier, wherein the Compound of Cycle I and the compound of Cycle II are administered sequentially. The composition may be present as a kit having each sequence in blister packs.

7 Claims, 1 Drawing Sheet

Table 1.

| Month | Subject 1<br>34 year old male | | | Subject 2<br>31 year old female | | | Subject 3<br>27 year old male | | |
|---|---|---|---|---|---|---|---|---|---|
| | Start | End | Calories | Start | End | Calories | Start | End | Calories |
| 1 | 227 | 222 | 1800 | 162 | 155 | 1500 | 270 | 265 | |
| 2 | 222 | 218 | 1800 | 155 | 150 | 1500 | 265 | 258 | |
| Weight change | Lost 9 lbs. | | | Lost 7 lbs. | | | Lost 12 lbs. | | |
| 3 | 218 | 218 | 2-3000 | 150 | 156 | 2-3000 | 258 | 262 | |
| 4 | 218 | 220 | 2-3000 | 156 | 158 | 2-3000 | 262 | 262 | |
| 5 | 220 | 224 | 2-3000 | 158 | 162 | 2-3000 | 262 | 268 | |
| 6 | 224 | 226 | 2-3000 | 162 | 165 | 2-3000 | 268 | 268 | |
| Weight change | Gained 8 lbs. | | | Gained 15 lbs. | | | Gained 10 lbs. | | |
| 7 | 226 | 218 | 1800 | 165 | 152 | 1500 | 268 | 258 | |
| 8 | 218 | 205 | 1800 | 152 | 138 | 1500 | 258 | 245 | |
| Weight change | Lost 21 lbs. | | | Lost 27 lbs | | | Lost 22 lbs. | | |

COMPOSITIONS AND METHODS FOR ENHANCING WEIGHT-LOSS BY CYCLICAL ADMINISTRATION OF COMPOUNDS

FIELD OF THE INVENTION

The present invention relates to a method for enhancing weight loss and to products and nutritional compositions suitable for use in such a method. More specifically, the invention relates to a method for the treatment of obesity by the sequential administration of at least one weight loss enhancing beta-adrenergic compound that is either a beta-adrenergic agonist or a beta-adrenergic partial agonist; and at least one weight loss enhancing adenylate cyclase receptor replenishing compound, in conjunction with a pharmaceutically acceptable diluent or carrier.

BACKGROUND OF INVENTION

The prevalence of obesity is rapidly increasing globally. Obesity is a serious health problem throughout the world. More than half of U.S. adults are overweight (61%) and more than a quarter (26%) of U.S. adults are obese. The inability of many individuals to keep their weight in check by diet and exercise has created a need for additional therapeutic means to combat obesity. Despite great effort, the pharmaceutical industry has not come up with the solution; because most weight-loss drugs to date have serious adverse effects to health and well-being.

Epidemiological studies have associated obesity with a range of cancer types, although the mechanisms by which obesity induces or promotes tumorigenesis vary by cancer site. These include insulin resistance and resultant chronic hyperinsulinaemia, increased bioavailability of steroid hormones and localized inflammation. Gaining a better understanding of the relationship between obesity and cancer can provide new insight into mechanisms of cancer pathogenesis. Calle E E, Kaaks R, 4(8) Nat Rev Cancer 579-91 (2004).

According to the Centers for Disease Control and Prevention, an astonishing two of every three American adults are overweight. Simply put, being overweight poses grave health risks for aging adults. Excess fat can unleash a cascade of pathological effects in the body, damaging every cell and organ system while increasing the risk of age-related health problems. Western society is increasingly concerned with personal weight and appearance. Diets and weight loss programs are extensively advertised and utilized by a large segment of Western society with varying degrees of effectiveness. There is a continuing search for new and effective means to facilitate weight loss.

Weight loss has become an industry to itself, with a number of well known and successful programs such as Jenny Craig, of Carlsbad, Calif. that offers packaged foods and weekly meetings and counseling; NutriSystem, Inc., of Horsham, Pa. that delivers packaged foods to the home and promotes a "low glycemic index"; South Beach Diet, of Miami, Fla., a book based program of two weeks of protein only followed by the slow inclusion of "good" fats and "good" carbohydrates; and Medifast, Inc., of Owings Mills, Md., an on-line program that instructs its participants to eat every 2 hours and offers shakes, bars, drinks, oatmeal, chili, soups, and puddings.

Attempts to facilitate weight loss and weight control are abundant, and include both pharmaceutical and nutraceutical compositions. U.S. Pat. Nos. 6,576,272 and 6,420,350 disclose methods of promoting fat loss by administering Citrus aurantium extract standardized for about 6% synephrine alkaloids, caffeine and hypericum, and U.S. Application No. 20060210650 discloses a weight loss composition having one of calcium and/or a salt of calcium and garcinia cambogia extract.

U.S. Application No. 20060182825 discloses a composition for reducing body fat having at least one plant-derived substance which inhibits adipogenesis in the body of said mammal; and b. at least one plant-derived substance which promotes lipolysis in the body of said mammal.

U.S. Pat. No. 6,447,818 discloses a weight loss composition of ephedrine pseudo-ephedrine, synephrine tyramine, octopamine, methyl tyramine, or horderine in combination with a Crataegus extract containing flavonoids and Gingko biloba extract. U.S. Pat. No. 5,422,352 discloses a method for reducing weight by administering ephedrine and caffeine in a weight ratio of about 1:12, calculated on the amount of ephedrine in the form of the free base; and U.S. Pat. No. 5,055,460 discloses a weight loss composition of ephedrine, caffeine and aspirin.

U.S. Pat. No. 6,784,206 discloses a method of manufacture of a soft-gel capsule comprising 1% Corosolic acid, wherein the Corosolic acid is absorbed into the intestinal tract of a human in order to sustain weight loss management and maintain blood sugar levels. Moreover, this patent purports to aim to improve high blood sugar levels in subjects suffering from non-insulin dependant diabetes mellitus.

Sequential Formulations

The use of more than one weight loss compounds that work through distinct mechanisms has been disclosed, though none are directed to the combination of a beta-3 adrenergic compound and an adenyl cyclate receptor replenishing compound. U.S. Pat. No. 6,403,641 discloses the use, simultaneously, separately or sequentially of sibutramine hydrochloride monohydrate and orlistat results in benefit on weight loss. Sibutramine is a 5-hyrdroxytryptamine and noradrenaline reuptake inhibitor and reduces body weight by decreasing food intake and enhancing satiety and stimulating thermogenesis. Orlistat inhibits lipase enzymes which are responsible for breaking down ingested fat.

Similarly, U.S. Pat. No. 5,716,976 discloses the sequential use of the genus of anorexic compounds for the treatment of carbohydrate addiction by administering to a human suffering from carbohydrate addiction a first anorexient or combination of anorexients in amounts sufficient to relieve the addiction for a period of time insufficient to develop tolerance to the administration; and then replacing said anorexient or combination of anorexients with an appropriate amount of a different anorexient or combination of anorexients. Most specifically the anorexients may be a serotonin agonist, a serotonin reuptake inhibitor, a norepinephrine agonist, phenylpropanolamine or others.

U.S. Pat. App. Nos. 20070105843 and 20070066601 disclose pharmaceutical composition that combine a serotonin reuptake inhibitor in combination with a 5-HT.sub.2C receptor antagonist, inverse agonist or partial agonist, adapted for sequential use, and methods for treating various psychiatric disorders by the administration of said composition. U.S. Pat. App. No. 20030130355 discloses a composition that combines serotonin reuptake inhibitor and/or a noradrenaline reuptake inhibitor and 5-HT.sub.1A agonist and methods to treat obesity. Different forms of 5-HT receptor agonists and antagonists and the like are combined in U.S. Pat. App. No. 20020068732.

Similar compositions and methods for treating various psychiatric disorders, U.S. Pat. App. No. 20060223857, 20050288355 and 20020103249 that combine a serotonin reuptake inhibitor, and another compound; diabetes, U.S. Pat.

App. No. 20060111428 and 20050059706; and digestive disorders, U.S. Pat. App. No. 20040191237.

A need continues to exist for improved weight loss compositions which are safe, effective and exhibit reduced side effects in humans. A new approach to weight loss composition and methods for use in humans is needed.

Excess insulin functions as a death hormone that devastates virtually every cell and organ system in the body. Insulin overload increases the risk of heart disease, cancer, blindness, stroke, Alzheimer's, and other age-related diseases. Heinbronn, L K, 295(13) JAMA 1577-8 (2006). The International Agency for Research on Cancer has determined that, based on results from epidemiological studies, people who are overweight or obese are at increased risk of developing several cancer types, including adenocarcinoma of the oesophagus, colon cancer, breast cancer in postmenopausal women, endometrial cancer, renal cancer and cancers of the liver, gallbladder and pancreas. Insulin resistance develops as a metabolic adaptation to increased levels of circulating free fatty acids released from adipose tissue, especially intra-abdominal adipose. Insulin resistance is generally compensated by increased pancreatic insulin secretion. There is mounting epidemiological and experimental evidence to indicate that chronic hyperinsulinaemia increases risk of cancers of the colon and endometrium, and probably other tumours. Successful intervention strategies for weight loss and maintenance at the individual and community level are needed to reduce cancer risk. Calle E E, Kaaks R, 4(8) Nat Rev Cancer 579-91 (2004).

The metabolic syndrome, a concurrence of disturbed glucose and insulin metabolism, overweight and abdominal fat distribution, mild dyslipidemia, and hypertension, is associated with subsequent development of type 2 diabetes mellitus and cardiovascular disease. Men with the metabolic syndrome were 2.9 times more likely to die of cardiovascular disease. Lakka, H M, et al, 288(21) JAMA. 2709-16 (2002). Similar results were observed by another group of researchers, who found that metabolic syndrome was associated with about a 2-fold increase in age-adjusted risk of fatal cardiovascular disease in men and nonfatal cardiovascular disease in women. Dekker, J M et al 112(5) Circulation. 666-73 (2005).

Adipose tissue, once thought to function primarily as a passive depot for the storage of excess lipid, is now understood to play a much more active role in metabolic regulation, secreting a variety of metabolic hormones and actively functioning to prevent deleterious lipid accumulation in other tissues and to modulate the insulin resistance. 21 Spec Med Sci (Paris) 10-8 (2005). White adipose tissue is now recognized as a major endocrine and secretory organ, releasing a wide range of protein factors and signals termed adipokines—in addition to fatty acids and other lipid moieties. A paradigm shift came with the discovery of leptin, a pleiotropic hormone which is a critical signal to the hypothalamus in the control of appetite and energy balance. A number of adipokines, including adiponectin, tumour necrosis factor-alpha, interleukin (IL)-1beta, IL-6, IL-8, IL-10, monocyte chemoattractant protein-1, macrophage migration inhibitory factor, nerve growth factor, vascular endothelial growth factor, plasminogen activator inhibitor-1 and haptoglobin, are linked to inflammation and the inflammatory response. Obesity is characterized by a state of mild inflammation, and the expression and release of inflammation-related adipokines generally rises as adipose tissue expands; a notable exception is adiponectin, with its anti-inflammatory action, the levels of which fall. White adipose tissue may be the main site of inflammation in obesity, increased circulating levels of inflammatory markers reflecting spillover from an 'inflamed' tissue, leading to the obesity-associated pathologies of type 2 diabetes and the metabolic syndrome. Trayhurn P, 184(4) Acta Physiol Scand. 285-93 2005). Scientists have identified more than 100 proteins, fatty acids, hormones, and inflammatory agents that are secreted by adipose tissue. Hauner H, 64(2) Proc Nutr Soc. 163-9 (2005).

Obesity, originally presumed to result from simple overeating or the combination of overeating with inactivity, has more recently been attributed to a genetic predisposition in combination with poor diet and exercise habits. It has been suggested that predisposition to obesity is associated with a defect in the sympathetic nervous system. This defect is manifested as a high efficiency in food utilization and a reduced thermogenic response to food intake. In normal persons, food intake results in a thermogenic response, that is, an increase in body temperature in which the caloric content of food is expended as heat. Some studies suggest that persons with a genetic predisposition to obesity are metabolically more efficient than lean persons, storing excess caloric energy as body fat. In obese persons, thermogenic defects may make a significant contribution to weight gain in the absence of controlled food intake. Calories not expended as heat are stored as excess weight. See Dulloo, A. G. and Miller, D. S., Wld. Rev. Nutr. Diet., vol. 50, pp. 1-56, 1987.

Pharmaceutical compositions have been developed with the purpose of stimulating thermogenesis and thereby inducing weight loss. The theory that beta agonists, especially beta 3 agonists, can affect body weight and fat mass is well accepted. Ephedrine has proven time and time again that it is an effective weight loss agent through its ability to increase thermogenesis and quench appetite. However, the publicity concerning adverse reactions has led to its gradual withdrawal from use by many despite the perceived consequences of obesity. Many companies are now substituting Citrus aurantium for ephedra in their formulations. Citrus aurantium, an agent containing beta agonists, has been reported to aid in weight loss in two studies and increase thermogenesis Preuss, et al 33(1-4) 1 J Med 247-64 (2002).

The theory that beta agonists, especially beta 3 agonists, can affect body weight and fat mass is well accepted. Preuss, et al 33(1-4) 1 J Med 247-64 (2002). Thermogenesis has been shown to be controlled by the beta-3 receptors of the adrenergic system. Hoeks, et al, 285 μm J Physiol Endocrinol Metab E775-E782 (2003).

SUMMARY OF THE INVENTION

This inventor has discovered that the beta-3-adrenergic receptor, like the beta-2 adrenergic receptor, is associated with thermogenesis and fat metabolism, and obese individuals are more prone than normals to have a particular genotype of this receptor. Subjects carrying the Gly16 or Arg64 alleles had significantly greater total fat-mass and waist-to-hip ratio at entry and over a 5-year period compared to the subjects who did not carry these polymorphisms. Subjects carrying the Gly16 allele had similar levels of plasma norepinephrine, higher levels of plasma leptin and a lower slope of the regression lines between plasma leptin and norepinephrine levels. Those carrying the Arg64 allele had higher plasma norepinephrine levels at entry and over a 5-year period compared to the subjects without the Arg64 allele, but plasma leptin levels and slopes were similar. The findings demonstrate that the Arg64 allele of the β 3-adrenoceptor polymorphisms relates to weight gain & minus; induced BP elevation accompanying high plasma norepinephrine in obese men. Kawaguchi et al, 29 (12) Hypertension Research 951-959 (2006). The beta3-adrenergic receptor is also associated with lipolysis. The presence of the beta(3)-adrenoceptor in human white adipocytes is consistent with evidence that it can mediate lipolysis in human white adipocytes. De Matteus, et al, 26(22) Int J Obes Relat Metab Disord 1442-50 (2002).

The breakdown of fat is influenced by beta-3-adrenergic receptors that are found in the fat itself. Conceptually, in the thermogenesis function, the Adrenergic Receptors and Uncoupling Proteins work together, having respectively, a regulatory and effector role. The ADRB2 activation induces lipolysis and release of non-esterified fatty acids whereas UCPs are regulated by NEFA plasma levels and are involved in their metabolism. Physiologically beta-3-adrenergic stimulation induces lipolysis and its polymorphic variants seem to influence this phenomenon. Pinelli M, et al, 7 BMC Med Genet 85 (2006).

This inventor has discovered, surprisingly, that by the sequential administration of nutritional compounds that operate by different mechanisms to enhance weight loss, specifically compounds that increase beta-3 adrenergic stimulation and other compounds that replenish the adenylate cyclase receptor through which the beta-3 receptor is stimulated, the long-felt need to avoid the usual "plateau effect" of most weight loss programs is accomplished. This is because persons become desensitized to a weight loss enhancing compound after several weeks. This is scientifically known as receptor attenuation or downgrade regulation. By interrupting the beta-2 and beta-3 adrenergic stimulation before their effects are down regulated with a regimen that supports and replenishes the receptor that is used in that stimulation, continuous weight loss can be achieved over longer periods than was previously possible.

The invention avoids the resistance to the compounds that affect the adipose cells during weight loss, which is known to occur when taking prescription medication or during any drastic body transformation such as weight loss. Once the body realizes that a human is trying to loose weight, it will fight back and you will plateau; weight loss ceases thereafter. This occurs in response to any long-term adipose cell receptor stimulation and other long-term pharmacotherapy, whether prescription drugs or supplements. Cell receptors, more specifically G protein receptors simply stop responding. In many cases, the adipose cells will limit and reduce the number of receptors that respond to fat breakdown. Unfortunately, most companies have developed weight loss products for years without addressing these two very important issues that lead to weight loss failure. Weight loss resistance mechanisms are well known but have not been addressed until know. This invention has solved the long-felt need to achieve weight loss without resistance or receptor attenuation.

The invention employs a revolutionary method of cycling on and off between powerful active ingredients. The invention comprises of two cycles of products. Cycle I is comprised of a beta-3 adrenergic compound, and Cycle II restores the adenylate cyclase receptors that were activated during the administration of Cycle I, and increases energy and satiety so that weight loss continues during Cycle II.

Chlorogenic Acid

Chlorogenic acid, another main constituent of coffee beans, has recently been reported to selectively inhibit hepatic glucose-6-phosphatase, which is a rate-limiting enzyme involved in gluconeogenesis. Further, the level of hepatic TG was significantly reduced by chlorogenic acid (60 mg/kg·day), suggesting its role in the suppression of hepatic TG in the group treated with green coffee bean extract. Shimoda, et al, 6 BMC Complement Altern Med 9 (2006).

The cell cycle assay indicated that the treatment of 3T3-L1 preadipocytes with chlorogenic acid, o-coumaric acid, and m-coumaric acid caused cell cycle arrest in the G1 phase. Hsu 54(12) J Agric Food Chem 4191-7 (2006).

Chlorogenic acid has been used to modifying "off" taste, U.S. Patent App. No. 20040213881 in artificially sweetened food, but it has yet to be used to promote or maintain weight loss.

Epigallocatechin Gallate (EGCG)

Epigallocatechin gallate (EGCG) is a catechin polyphenol found in green and black tea. Green tea, camellia sinensis, is its usual source.

Adipocyte apoptosis has also been induced in vitro using tumor necrosis factor-alpha (TNF-alpha), (−)-epigallocatechin gallate (EGCG) from Camellia sinensis and ajoene, from Allium sativum. Natural products have potential for inducing apoptosis of adipose tissue, inhibiting bone marrow adipogenesis and increasing the expression of osteogenic factors in bone, thereby yielding effective treatments for obesity and osteoporosis. Nelson-Dooley C, Curr Med Chem. 12(19) Curr Med Chem 2215-25 (2005).

Epigallocatechin gallate (EGCG, 4 approximately 12 microg/mL) did not affect the contractile responses evoked by phenylephrine and high K+. GTE (5 approximately 20 mg/kg) given into a femoral vein of the normotensive rat produced a dose-dependent depressor response, which is transient. Interestingly, the infusion of a moderate dose of GTE (10 mg/kg/30 min) made a significant reduction in pressor responses induced by intravenous norepinephrine. Lim, Dy et al 26(3) Arch Pharm Res. 214-23 (2003).

The benefits of EGCG in weight loss and weight loss maintenance, both as a compound and as part of an extract of Green or Black Tea, and as a component of the tea has been studied. Weight loss compositions using EGCG include other nutrients that promote weight loss, including caffeine U.S. Pat. Application No. 20060252706, as green tea extract containing 20%-50% epigallocatechol gallate with or without caffeine, U.S. Pat. App. Nos. 20030104081; with caffeine and in combination with a low glycemic supplement, 5-hydroxytryptophan (5-HTP), and chromium, U.S. Pat. App. Nos. 20060159724, 20030143287, 20030143287 and 20060159724; in combination with other nutritional supplements or foods such as kidney beans and extracts, U.S. Pat. App. No. 20070065500; or raspberry ketone, 4-(4-hydroxyphenyl)-2-butan-one, U.S. Pat. App. Nos. 20050288360 and 20050288360; linoleic acid, U.S. Pat. App. Nos. 20040202732 and 20040202732; a compound that enhances serotonin-mediated neurotransmission, U.S. Pat. App. Nos. 20030162725 and 20030162725

Naringenin

AcylCoA-cholesterol-o-acyltransferase (ACAT) is inhibited in a mammal which comprises administering an effective amount of naringin or naringenin. Methods are provided for inhibiting the activity of acylCoA-cholesterol-o-acyltransferase, inhibiting the accumulation of macrophage-lipid complex on the arterial endothelium, and preventing or treating hepatic diseases in a mammal comprise administering naringin or naringenin thereto. This enzyme metabolizes cholesterol into S-Methyl Malonyl CoA. Acyl CoA-cholesterol-o-acyltransferase (ACAT) promotes the esterification of cholesterol in blood. Foam cells are formed by the action of ACAT and contain a large amount of cholesterol ester carried by low density lipoproteins. The formation of foam cells on the wall of artery increases with the ACAT activity, and, accordingly, an inhibitor of ACAT may also be an agent for preventing atherosclerosis. Bok, U.S. Pat. No. 6,165,984.

Other flavonoids (naringenin, silibinin, silymarin and taxifolin, 100-200 mg kg-1) reduced (23-41%; P<0.05-0.01) intestinal transit at doses of 100-200 mg kg-1 while hesperitin, catechin and phloridzin (up to 200 mg kg-1) had no effect. It is suggested that these effects, influenced by the structure of the molecules, are mediated by alpha 2-adrenergic receptors and calcium. Di Carlo, G, et al, 45(12) J Pharm Pharmacol 1054-9 (1993).

Naringenin (aglycone of naringin) (2×10(−6) and 1×10(−7) M) increased the contractile effect of noradrenaline and the maximal effect evoked was related to the maximal dose of naringenin. 4. The alpha 2 antagonism produced by yohimbine in the naringenin-noradrenaline association were retained at two doses of naringenin tested and we noticed a similar behavior when we used clonidine-noradrenaline. Herrera M D, and Marhuenda E, 24(3) Gen Pharmacol 739-42 (1993).

Evodiamine

U.S. Pat. Nos. 5,998,421 and 6,214,831 disclose a food and methods for improving lipid metabolism or preventing or treating obesity by administering an evodiamine compound. Evodia rutaecarpa (ER) and Tetradium glabrifolium (TG) are closely related species collected from different locations, with processed versus unprocessed and fresh versus 1-year-old samples. The purpose of this study is to determine the variability of their bioactive constituents; evodiamine, dehydroevodiamine, rutaecarpine and synephrine—as well as their relaxing effects on an isolated rat aortas and uterus using the extracts of the test specimens. The vasorelaxation was greater in ER from Taiwan than from China in spite of lower levels of the relaxing alkaloids evodiamine, dehydroevodiamine and rutaecarpine. On the other hand, the uterine relaxation of ER from China was better than the one from Taiwan, even though constricting synephrine was only contained in Chinese ER. Ko HC, 108(2) J Ethnopharmacol 257-63 (2006)

The Ko study suggests a Beta-2-adrenergic effect since such an effect has been established as the mechanism for uterine relaxation. It is proposed that the beta adrenoceptor-linked relaxation results from the concerted effects of both a cyclic AMP-dependent (sensitive to low cyclic AMP) and a cyclic AMP-independent process; the latter is postulated to operate at the membrane level with an ultimate reduction in cytosolic Ca++. On the other hand, cyclic AMP, provided it reached a critical concentration essential to mediate intracellular Ca++ sequestration, would be the sole determinant for forskolin-elicited relaxation. It is proposed that the beta adrenoceptor-linked relaxation results from the concerted effects of both a cyclic AMP-dependent (sensitive to low cyclic AMP) and a cyclic AMP-independent process; the latter is postulated to operate at the membrane level with an ultimate reduction in cytosolic Ca++. On the other hand, cyclic AMP, provided it reached a critical concentration essential to mediate intracellular Ca++ sequestration, would be the sole determinant for forskolin-elicited relaxation. Do Khac L, Mokhtari A, Harbon S, 239(1) J Pharmacol Exp Ther 236-42 (1986)

Evodiamine has additionally been shown to stimulate catecholamine secretion from bovine adrenal medulla but also reversed insensitivity of these cells to acetylcholine or high K+ stimulation. Yoshizumi M, 44(1-2) J Med Invest 79-82 (1997)

Beta-adrenergic effects are further supported by the inotropic cardiac and aortic vasodilatory effects of evodia rutaecarpa.

The crude acetone extract of the fruits of Evodia rutaecarpa Bentham (Rutaceae) exhibited a positive inotropic effect on the guinea pig isolated left atria. The extract was subject to bioassay-directed fractionation to yield the powerful cardiotonic agent evodiamine. The positive inotropic and chronotropic effects of evodiamine and rutaecarpine, indoloquinazoline alkaloids isolated from the fruits of Evodia rutaecarpa, on the guinea-pig isolated right atria: possible involvement of vanilloid receptors. Shoji M, 75(6) J Pharm Sci 612-3 (1986).

Inotropic effects are controlled by the beta-2-adrenergic receptor. The rapid and dose dose-dependent phosphorylation of both p38 and p42/44 MAPKs has been shown for beta-2 adrenergic agonists. Magne S and Pavoine C 276(43) J. Biol. Chem 39539-39548 (2001).

The vasoreactivity of dehydroevodiamine (1), evodiamine (2), and rutaecarpine (3), quinazoline alkaloids isolated from Evodia rutaecarpa, to aorta smooth muscle demonstrated that they produce a vasodilatory effect on endothelium-intact rat aorta with equal potency. Chiou W F, Liao J F and Chen C F, 59(4) J Nat Prod 374-8 (1996).

Nitric oxide-dependent beta-2-adrenergic dilation of rat aorta is mediated through activation of both protein kinase A and Akt. Ferrol A, et al, 143 British Journal of Pharmacology 397-403 (2004).

Caffeine

Caffeine has been shown to be beta-adrenergic. Yun, A J, Doux J N, Daniel, S M, 68(1) Med Hypothese 31-6 (2007). During steady state conditions (last hour of the test) after ingestion of caffeine, lipid turnover increased 2-fold (P<0.005), and the mean (+/−SEM) thermic effect was 13.3+/−2.2% (P<0.001), both of which were greater than after ingestion of placebo or caffeine during beta-adrenoceptor blockade. After ingestion of caffeine, oxidative FFA disposal increased 44% (236+/−21 to 340+/−16 micro mol/min), whereas non-oxidative FFA disposal increased 2.3-fold (455+/−66 to 1054+/−242 micro mol/min; P<0.01). In postabsorptive conditions, 34% of lipids were oxidized and 66% were recycled. Caffeine ingestion increased energy expenditure 13% and doubled the turnover of lipids, of which 24% were oxidized and 76% were recycled. beta-adrenoceptor blockade decreased, but did not inhibit, these variables. The authors concluded that many, but not all, of the effects of caffeine are mediated via the sympathetic nervous system. Acheson K J, 79(1) Am J Clin Nutr. 40-6 (2004).

Caffeine, in combination with other nutrients, has been disclosed for the treatment of obesity. As one example, U.S. Pat. App. Nos. 20060078627 and 20060078627 teach the combination of caffeine and phenylalanine, with 5-hydroxytryptophan and L-tryptophan as a composition for use in obesity.

Synephrine

The activities of the (−)- and (+)-forms of—and p-octopamine and—and p-synephrine on beta 1- and beta 2-adrenoceptors in guinea-pig atria and trachea have been compared with that of noradrenaline. Jordan R et al, 39(9) J Pharm Pharmacol. 752-4 (1987). Synephrine has also been used for topical use, for external body part or organ slimming, firming, cellulite reduction. U.S. Pat. App. No. 20040185069.

The use of epigallocatechol gallate (EGCG), the catechol rich extract of green tea, and caffeine, has been disclosed as useful in the treatment of obesity and fat metabolism by Rhombi, U.S. Pat. Nos. 6,814,986 and 6,830,765. U.S. Pat. App. No. 20020058075 discloses the use of synephrine and other materials derived from citrus for weight loss. Citrus aurantium (bitter orange) is a plant belonging to the family Rutaceae, whose fruit extracts have been used recently for the treatment of obesity. Synephrine may be present in the peel and the edible part of Citrus fruit. Pellati F, Benvenuti S, 1161(71-88) J Chromatogr A. 2007.

Caffeine is found in the composition disclosed by US Application 20050025844 that additionally includes an adrenergic amine, which may be synephrine or hordenine, forskolin, guggulsterone, alpha-2 receptor antagonist, and vinca alkaloid.

Cyclic Adenosine Monophosphatase

Cyclic adenosine monophosphate (cAMP, cyclic AMP or 3'-5'-cyclic adenosine monophosphate) is a molecule that is important in many biological processes; it is derived from adenosine triphosphate (ATP). cAMP controls many biological processes, including glycogen decomposition into glucose (glycogenolysis), and lipolysis.

cAMP is synthesized from ATP by adenylate cyclase which is located at the cell membranes at receptors coupled to heterotrimeric G proteins that include the beta adrenergic receptors. Biochemical Pathways, Map No. U3 V3, www.exPASy.com, Courtesy of Roche Applied Science, (c) 1993 Boehringer Mannheim GmbH—Biochemica. Adenylate cyclase is activated by the hormones glucagon and adrenaline through the activation of adenylate cyclase stimulatory G (Gs)-coupled receptors and inhibited by agonists of adenylate cyclase inhibitory G (Gi)-protein coupled receptors.

cAMP is a second messenger, used for intracellular signal transduction, such as transferring the effects of hormones like glucagon and adrenaline, which cannot get through the cell membrane. Its main purpose is the activation of protein kinases; it is also used to regulate the passage of $Ca^{2+}$ through ion channels.

Epinephrine (adrenaline) binds its receptor, that associates with an heterotrimeric G protein. The G protein associates with adenylate cyclase that converts ATP to cAMP, spreading the signal.

B12 Vitamins

According to this invention, the B12 vitamins, cyanocobalamin, methylcobalamin, and S-adenosylcobalamin help to stabilize the receptor site during the second cycle, and cyclic adenosine monophosphate (cAMP) also supports the receptor and promotes energy and satiety.

Vitamin B 12 deficiency results in the impairment of the coupling among the beta-adrenoceptor, G5- and the catalytic subunit of adenylyl cyclase, and in dysfunction of the catalytic subunit of the enzyme, suggesting that vitamin B 12 participates in the regulation of neuronal adenylate cyclase signal transduction. Hatta, S, et al, 291(3) Eur J Pharmacol 351-8 (1995).

The subcellular localization of G5 alpha, Gi alpha 1&2, Gi alpha 3, and G beta was studied in primary-cultured undifferentiated and differentiated, lipid replete, adipose cells. The results show a distinct distribution for each of these G-proteins and differences between differentiated and undifferentiated cells. All the G-proteins examined had a cytoplasmic localization; only Gi alpha 1 and 2 showed a significant co-localization with the plasma membrane and this only in differentiated cells. Most studies using cells in culture have reported an intracellular localization for G-proteins, whereas in tissue sections the localization has been reported to be largely with the plasma membrane, with some intracellular localization. The results suggest that the cell-cell interactions or the specific geometry imposed by culture conditions favor the intracellular compared to peripheral localization of G-proteins. In adipose tissue plasma membranes, G proteins regulate the lipolytic response to catecholamines by modulating acetylcholine mediated production of C-AMP. Begin-Heick N et al, 65(2) J Cell Biochem 65(2):259-66 (1997).

For the beta 2-adrenergic receptor (beta 2AR) system, which is coupled to adenylate cyclase via the stimulatory guanine nucleotide-binding regulatory (G5) protein, homologous desensitization is mediated in part by a receptor-specific kinase (beta ARK) and a soluble cofactor (beta-arrestin). Bliziotes M, Murtagh J, and Wiren K 11(6) J Bone Miner Res 820-6 (1996).

BRIEF DESCRIPTION OF THE DRAWINGS

Table 1: Data including weights at the beginning of each month, change in weight for each regimen, and average calorie intake for three subjects observing the following weight loss regimen:

months 1-2: reduced calorie diet and exercise for 30 minutes three times per week;

months 3-6: no diet or exercise regimen months 7-8: Cyclical administration of a first weight loss composition and a second weight loss composition, combined with a reduced calorie diet and exercise 30 minutes three times per week. The first weight loss composition comprises 100 mg epigallocatechin gallate, 50 mg chlorogenic acid, 125 mg caffeine, 10 mg synephrine, 10 mg evodiamine, and 5 mg naringen. The second weight loss composition comprises 3 mg cyanocobalamin, 1 mg methylcobalamin, 1 mg S-adenosylcobalamin, and 1 mg cyclic adenosine monophosphate.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In the Summary above, the Description of the Invention, and the Claims and Abstract below, reference may be made to particular features (including method steps) of the invention. It is to be understood that this disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number or the indefinite article "a" (meaning "one") is used herein to denote the start of a range beginning with that number (which may be a range having an upper limit or no upper limit, depending on the variable being defined). For example "at least one" or "at least a" means 1 or more than 1. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. If, in this disclosure, a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm.

The term "or" is used herein as a conjunction used to link alternatives in a series of alternatives. The term "and/or" is used herein as a conjunction meaning that either or both of two options may be valid.

Accordingly, the present invention, according to an embodiment thereof, is directed towards a method for the enhancement of weight loss in a human which comprises; a. administering to a human seeking to lose weight at least one weight loss enhancing nutrient of Cycle I selected from the group consisting of beta-3-adrenergic agonists and partial agonists in amounts sufficient to stimulate the beta-3-adrenergic receptors for a period of time I insufficient to develop tolerance to the administration; and b. then replacing said at least one weight loss enhancing nutrient of Cycle I with an appropriate amount of at least one weight loss enhancing nutrient of Cycle II that maintains the adenylate cyclase receptor and administering said weight loss enhancing nutrient that maintains the adenylate cyclase receptor for a period of time sufficient to re-establish the body's response to Cycle I; and c. repeating steps a. and b. over and over; whereby weight loss is promoted, for as long as the weight loss regimen continues. Once weight loss is achieved, weight can be maintained by continued cycling of products.

The periods of time I and II may be of any therapeutically effective period, most specifically between about 1 week to about 3 months for periods of time I and II is about 1 week to about 3 months. Most specifically, the beta-3 adrenergic compound is administered for about 21 days and the adenylate cyclase receptor replenishing compound is administered for about 7 days.

The beta-3 adrenergic compound may be at least one of epigallocatechin gallate, chlorogenic acid, caffeine, synephrine, evodiamine and naringenin, and the enantiomers and pharmaceutically acceptable salts thereof and the at the adenylate cyclase replenishing compound is one or more of cyanocobalamin, methylcobalamin, S-adenosylcobalamin and cyclic adenosine monophosphate.

The amount of each compound to be administered will depend on a number of factors including the age of the patient, the severity of the condition and the past medical history of the patient and always lies within the sound discretion of the administering physician but it is generally envisaged that the dosage of the compound of the method of the invention is performed with a composition in which epigallocatechin gallate may be present in an amount of about 100 mg; chlorogenic acid may be present in an amount of about 50 mg; caffeine may be present in amount of about 125 mg; synephrine may be present in an amount of about 10 mg; evodiamine may be present in an amount between about 10 mg; naringenin may be present in an amount of about 5 mg; cyanocobalamin may be present in an amount of about 3 mg; methylcobalamin may be present in an amount of about 1 mg; S-adenosylcobalamin may be present in an amount of about 1 mg, cyclic adenosine monophosphate may be present in an amount of about 1 mg.

The human may be any human seeking to enhance weight loss, whether suffering from obesity, seeking to reduce body weight by a moderate amount, or merely seeking to maintain a normal and healthy weight.

The present invention may provide the following advantages. Firstly, the maximum weight loss achieved is greater than that achieved by the sole administration of either a compound of Cycle I or Cycle II. Secondly, a synergistic weight loss is achieved in which the weight loss obtained by the administration of a compound of Cycle I and the compound of Cycle II to a first test group is greater than the total weight loss achieved by administration of the compound of Cycle I to a second test group and the weight loss achieved by administration of Cycle II to a third test group. Thirdly, before weight loss reaches a plateau with administration of Cycle I, Cycle II is administered to promote further weight loss thus avoiding receptor cell attenuation. Fourthly, lower doses of the compound of Cycle I and the compound of Cycle II may be used in the present invention thus reducing the side-effects associated with administration of a higher dose of each compound.

In another aspect the present invention provides a compound of Cycle I and a compound of Cycle II that may be enantiomers and pharmaceutically acceptable salts thereof, administered in sequential use for the treatment of obesity.

The invention also provides the use of the above combination of drugs in the manufacture of a medicament for the treatment of obesity. Additionally, it provides the combination for use in the treatment of obesity.

Any of the compositions provided may be used in the method of enhancing weight loss in a human in need thereof.

In a first group of embodiments the composition of the present invention may include a combination of Cycle I, wherein the combination includes at least one weight loss enhancing compound other than an adenylate cyclase receptor replenishing compound; and at least one weight loss enhancing adenylate cyclase receptor replenishing compound of Cycle II, in conjunction with a pharmaceutically acceptable diluent or carrier, wherein the compound of Cycle I and the compound of Cycle II are administered sequentially. In this embodiment, any weight loss enhancing compound may be used during 21 of every 28 days, so long as the Cycle II compound is used during the remaining 7 days.

In a preferred embodiment, the at least one weight loss enhancing compound of Cycle II is selected from the group consisting of one or more of cyanocobalamin, methylcobalamin, S-adenosylcobalamin and cyclic adenosine monophosphate.

In a more preferred embodiment, said cyanocobalamin, if present may be present in an amount between 0.1 mg and 50 mg; said methylcobalamin, if present, may be present in an amount between 0.1 mg and 50 mg; said S-adenosylcobalamin, if present, may be present in an amount between 0.1 mg and 50 mg; said cyclic adenosine monophosphate, if present may be present in an amount between 0.1 mg and 10 mg.

More specifically, the cyanocobalamin, if present may be present in an amount between 1 mg and 10 mg; said methylcobalamin, if present, may be present in an amount between 0.5 mg and 25 mg; said S-adenosylcobalamin, if present, may be present in an amount between 0.5 mg and 25 mg; said cyclic adenosine monophosphate, if present may be present in an amount between 0.3 mg and 5 mg.

In a most preferable embodiment, the cyanocobalamin, if present, may be present in an amount of about 3 mg; the methylcobalamin, if present, may be present in an amount of about 1 mg; said S-adenosylcobalamin, if present, may be present in an amount of about 1 mg, said cyclic adenosine monophosphate may be present in an amount of about 1 mg.

In another preferred embodiment, the weight loss enhancing compound of Cycle II comprises cyanocobalamin, methylcobalamin, S-adenosylcobalamin and cyclic adenosine monophosphate.

In a more preferred embodiment, the cyanocobalamin may be present in an amount between 0.1 mg and 50 mg; said methylcobalamin may be present in an amount between 0.1 mg and 50 mg; said S-adenosylcobalamin may be present in an amount between 0.1 mg and 50 mg; said cyclic adenosine monophosphate may be present in an amount between 0.1 mg and 10 mg.

More specifically said cyanocobalamin may be present in an amount between 1 mg and 10 mg; said methylcobalamin may be present in an amount between 0.5 mg and 25 mg; said S-adenosylcobalamin may be present in an amount between 0.5 mg and 25 mg; and the cyclic adenosine monophosphate may be present in an amount between 0.3 mg and 5 mg.

In a most preferred embodiment, the cyanocobalamin may be present in an amount of about 3 mg; said methylcobalamin may be present in an amount of about 1 mg; said S-adenosylcobalamin may be present in an amount of about 1 mg, said cyclic adenosine monophosphate may be present in an amount of about 1 mg.

In yet another embodiment, the composition is in a dosage form selected from the group consisting of a tablet, capsule, liquid, liposome, inhalant, sublingual tablet, suppository, oral spray and dermal patch.

In a second group of embodiments the composition of the present invention may include a combination, wherein the combination includes one or more of, without being limited to, at least one weight loss enhancing beta-adrenergic compound of Cycle I, wherein the compound is selected from the group consisting of beta-3-adrenergic agonists and beta-3-adrenergic partial agonists; and one or more of a weight loss enhancing adenylate cyclase receptor replenishing compound of Cycle II, in conjunction with a pharmaceutically acceptable diluent or carrier, wherein the Cycle I and the compound of Cycle II are administered sequentially.

In a preferred embodiment, the composition of the present invention may include a combination, wherein the combination includes one or more of, without being limited to the weight loss enhancing compound of Cycle I is one or more of, without being limited to, epigallocatechin gallate, chlorogenic acid, caffeine, synephrine, evodiamine or naringenin, and/or their enantiomers and pharmaceutically acceptable salts and one weight loss enhancing compound of Cycle II is one or more of, without being limited to, cyanocobalamin, methylcobalamin, S-adenosylcobalamin and/or cyclic adenosine monophosphate.

In a more preferred embodiment, the composition of the present invention may include the use of a combination, wherein the combination includes one or more of, without being limited to epigallocatechin gallate, which if present, may be present in an amount between about 10 mg and about 1000 mg; the chlorogenic acid, if present, may be resent in an amount between about 5 mg and about 500 mg; the caffeine, if present, may be present in amount between 12 mg and 1200 mg; the synephrine if present, may be present in an amount between about 1 mg to about 100 mg; the evodiamine, if present may be present in an amount between about 1 mg and about 100 mg; the naringenin if present, may be present in an amount between 1 mg and 100 mg; said cyanocobalamin, if present may be present in an amount between 0.1 mg and 50 mg; the methylcobalamin, if present, may be present in an amount between 1 mcg and 50 mg; the S-adenosylcobalamin, if present, may be present in an amount between 1 mcg and 50 mg; the cyclic adenosine monophosphate, if present may be present in an amount between 0.1 mg and 10 mg.

More specifically, the epigallocatechin gallate, if present, may be present in an amount between about 50 mg and about 500 mg; the chlorogenic acid, if present, may be present in an amount between about 25 mg and about 250 mg; the caffeine, if present, may be present in amount between 60 mg and 600 mg; the synephrine if present, may be present in an amount between about 5 mg to about 50 mg; the evodiamine, if present may be present in an amount between about 5 mg and about 50 mg; the naringenin if present, may be present in an amount between 5 mg and 50 mg; the cyanocobalamin, if present, may be present in an amount between 1 mg and 10 mg; the methylcobalamin, if present, may be present in an amount between 5 mcg and 25 mg; the S-adenosylcobalamin, if present, may be present in an amount between 5 mcg and 25 mg; the cyclic adenosine monophosphate, if present may be present in an amount between 0.3 mg and 5 mg.

In the most preferred embodiment, the present invention may include the use of a combination, wherein the combination includes one or more of, without being limited to, the epigallocatechin gallate, if present, may be present in an amount of about 100 mg; the chlorogenic acid, if present, may be present in an amount of about 50 mg; the caffeine, if present, may be present in amount of about 125 mg; the synephrine if present, may be present in an amount of about 10 mg; the evodiamine, if present, may be present in an amount of about 10 mg; the naringenin, if present, may be present in an amount of about 5 mg; the cyanocobalamin, if present, may be present in an amount of about 3 mg; the methylcobalamin, if present, may be present in an amount of about 1 mg; the S-adenosylcobalamin, if present, may be present in an amount of about 1 mg, the cyclic adenosine monophosphate may be present in an amount of about 1 mg.

In a yet another embodiment, the present invention may include the use of a combination, wherein the combination includes one or more of, without being limited to The weight loss enhancing compound of Cycle I comprises epigallocatechin gallate, chlorogenic acid, caffeine, synephrine, evodiamine, and naringen and said weight loss enhancing compound of Cycle II comprises cyanocobalamin, methylcobalamin, S-adenosylcobalamin and cyclic adenosine monophosphate.

In yet another and alternative of the fifth embodiment, the epigallocatechin gallate may be present in an amount between about 10 mg and about 1000 mg; the chlorogenic acid may be present in an amount between about 5 mg and about 500 mg; the caffeine may be present in amount between 12 mg and 1200 mg; the synephrine may be present in an amount between about 1 mg to about 100 mg; the evodiamine may be present in an amount between about 1 mg and about 100 mg; the naringenin may be present in an amount between 1 mg and 100 mg; the cyanocobalamin may be present in an amount between 0.1 mg and 50 mg; the methylcobalamin may be present in an amount between 0.1 mg and 50 mg; the S-adenosylcobalamin may be present in an amount between 0.1 mg and 50 mg; the cyclic adenosine monophosphate may be present in an amount between 0.1 mg and 10 mg. In another more specific embodiment, the epigallocatechin gallate may be present in an amount between about 50 mg and about 500 mg; the chlorogenic acid, may be present in an amount between about 25 mg and about 250 mg; the caffeine is present in amount between 60 mg and 600 mg; the synephrine is present in an amount between about 5 mg to about 50 mg; the evodiamine may be present in an amount between about 5 mg and about 50 mg; the naringenin may be present in an amount between 5 mg and 50 mg; the cyanocobalamin-may be present in an amount between 1 mg and 10 mg; the methylcobalamin may be present in an amount between 0.5 mg and 25 mg; the S-adenosylcobalamin may be present in an amount between 0.5 mg and 25 mg; the cyclic adenosine monophosphate may be present in an amount between 0.3 mg and 5 mg.

In its most specific alternative fifth embodiment, the epigallocatechin gallate may be present in an amount of about 100 mg; the chlorogenic acid may be present in an amount of about 50 mg; the caffeine may be present in amount of about 125 mg; the synephrine may be present in an amount of about 10 mg; the evodiamine may be present in an amount between about 10 mg; the naringenin may be present in an amount of about 5 mg; the cyanocobalamin may be present in an amount of about 3 mg; the methylcobalamin may be present in an amount of about 1 mg; the S-adenosylcobalamin may be present in an amount of about 1 mg, the cyclic adenosine monophosphate may be present in an amount of about 1 mg.

The composition is provided in any dosage form well known to those of ordinary skill in the art, specifically as a tablet, capsule, liquid, liposome, inhalant, sublingual tablet, suppository, oral spray and dermal patch.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacist's art. Tablets may be prepared from a mixture of the active compounds with fillers, for example calcium phosphate; disintegrating agents, for example maize starch; lubricating agents, for example magnesium stearate; binders, for example microcrystalline cellulose or polyvinylpyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound.

Other dosage forms for oral administration include, for example, aqueous suspensions containing the active compounds in an aqueous medium in the presence of a non-toxic suspending agent such as sodium carboxy-methylcellulose, and oily suspensions containing the active compounds in a suitable vegetable oil, for example coconut oil.

Dosage forms of the compounds of Cycle I and Cycle II suitable for rectal administration are the known pharmaceutical forms for such administration, for example, suppositories.

The compounds of Cycle I and Cycle II may be formulated into a composition which is dispersed as an aerosol into the patients oral or nasal cavity. Such aerosols may be administered from a pump pack or from a pressurised pack containing a volatile propellant.

Furthermore, the dosage form of the diet supplement in accordance with these embodiments may be provided in accordance with customary processing techniques for herbal and/or dietary supplements in any of the forms mentioned above.

In a specific embodiment, the composition is provided as a Kit, which is a packaged combination of at least one weight loss enhancing beta-2 or beta-3-adrenergic compound of Cycle I, wherein said compound is selected from the group consisting of beta-3-adrenergic agonists and beta-3-adrenergic partial agonists; and at least one weight loss enhancing compound that supports the adenylate cyclase receptor replenishing compound of Cycle II, in conjunction with a pharmaceutically acceptable diluent or carrier; instructions for a patient to carry out drug administration to achieve weight loss, wherein the compound of Cycle I and compound of Cycle II are present in separate and discrete dosage forms. In the Kit, the compound of Cycle I is present as 21 caplets in blister packages, and the compound of Cycle II is present as 7 liquid ampules, packaged in flexible packaging. The Kit instructs the user which compound to take on a daily and weekly basis. Alternatively, the compounds may be provided as tablets, powder, sublingual lozenges, suppositories, and the like.

The weight loss enhancing compound of Cycle I is epigallocatechin gallate, chlorogenic acid, caffeine, synephrine, evodiamine, and naringen and the weight loss enhancing compound of Cycle II comprises cyanocobalamin, methylcobalamin, S-adenosylcobalamin and cyclic adenosine monophosphate. The ingredients of the compound may be in any amount, most specifically those of the specific embodiments of the composition provided. Most specifically, epigallocatechin gallate is present in an amount of about 100 mg; the chlorogenic acid is present in an amount of about 50 mg; the caffeine is present in amount of about 125 mg; the synephrine is present in an amount of about 10 mg; the evodiamine is present in an amount between about 10 mg; the naringenin is present in an amount of about 5 mg; the cyanocobalamin is present in an amount of about 3 mg; the methylcobalamin is present in an amount of about 1 mg; the S-adenosylcobalamin is present in an amount of about 1 mg, and the cyclic adenosine monophosphate is present in an amount of about 1 mg.

Example 1

Three subjects, a 34 year old man, a 31 year old woman, and a 27 year old man, seeking to lose weight observed the following regimen for a period of eight (8) weeks:

During the first 8 week period, they did not use any weight loss supplements but maintained an reduced calorie per day diet and exercised 3 times a week for 30 minutes.

Following the 8 week period, they discontinued the diet and exercise regiment and ingested 2,000-3,000 calories per day for 17 weeks.

A second 8 week period then commenced during which he resumed the regimen of cyclical administration of the composition described above, a reduced calorie per day diet, and exercise 3 times a week for 30 minutes.

The subjects ingested epigallocatechin gallate in an amount of about 100 mg per day; chlorogenic acid an amount of about 50 mg per day; caffeine in amount of about 125 mg per day; synephrine an amount of about 10 mg per day; evodiamine is present in an amount of about 10 mg per day; and naringenin in an amount of about 5 mg for three weeks; maintained an 1,800 calorie per day diet and exercised 3 times a week for 30 minutes during the first three weeks.

During the fourth week, the subjects ingested cyanocobalamin in an amount of about 3 mg per day; methylcobalamin present in an amount of about 1 mg per day; S-adenosylcobalamin in an amount of about 1 mg per day, and cyclic adenosine monophosphate in an amount of about 5 mg per day for one week and maintained a reduced calorie per day diet and exercised 3 times a week for 30 minutes.

Data from the three subjects, including their weights at the beginning of each month, the change in weight for each regimen, and their average caloric intake during those regimens is depicted in

TABLE 1

| Month | Subject 1 34 year old male | | | Subject 2 31 year old female | | | Subject 3 27 year old male | | |
|---|---|---|---|---|---|---|---|---|---|
| | Start | End | Calories | Start | End | Calories | Start | End | Calories |
| 1 | 227 | 222 | 1800 | 162 | 155 | 1500 | 270 | 265 | |
| 2 | 222 | 218 | 1800 | 155 | 150 | 1500 | 265 | 258 | |
| Weight change | Lost 9 lbs. | | | Lost 7 lbs. | | | Lost 12 lbs. | | |
| 3 | 218 | 218 | 2-3000 | 150 | 156 | 2-3000 | 258 | 262 | |
| 4 | 218 | 220 | 2-3000 | 156 | 158 | 2-3000 | 262 | 262 | |
| 5 | 220 | 224 | 2-3000 | 158 | 162 | 2-3000 | 262 | 268 | |
| 6 | 224 | 226 | 2-3000 | 162 | 165 | 2-3000 | 268 | 268 | |
| Weight change | Gained 8 lbs. | | | Gained 15 lbs. | | | Gained 10 lbs. | | |
| 7 | 226 | 218 | 1800 | 165 | 152 | 1500 | 268 | 258 | |
| 8 | 218 | 205 | 1800 | 152 | 138 | 1500 | 258 | 245 | |
| Weight change | Lost 21 lbs. | | | Lost 27 lbs | | | Lost 22 lbs. | | |

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for enhancing weight loss in a human, which comprises;
   a. administering to a human seeking to lose weight at least one weight loss enhancing nutrient of Cycle I selected from the group consisting of epigallocatechin gallate, chlorogenic acid, caffeine, synephrine, evodiamine and naringenin, and the enantiomers and pharmaceutically acceptable salts thereof for a period of time insufficient to develop tolerance to the administration; and
   b. then replacing said at least one weight loss enhancing nutrient of Cycle I with an appropriate amount of at least one weight loss enhancing nutrient of Cycle II that maintains the adenylate cyclase receptor selected from the group consisting of one or more of cyanocobalamin, methylcobalamin, S-adenosylcobalamin and cyclic adenosine monophosphate and administering said weight loss enhancing nutrient that maintains the adenylate cyclase receptor for a period of time insufficient to develop tolerance to the administration; and
   c. repeating steps a. and b. over and over; whereby weight loss is promoted, for as long as the weight loss regimen continues.

2. The method of claim 1 wherein said epigallocatechin gallate is present in an amount of about 100 mg; said chlorogenic acid is present in an amount of about 50 mg; said caffeine is present in amount of about 125 mg; said synephrine is present in an amount of about 10 mg; said evodiamine is present in an amount between about 10 mg; said naringenin is present in an amount of about 5 mg; said cyanocobalamin is present in an amount of about 3 mg; said methylcobalamin is present in an amount of about 1 mg; said S-adenosylcobalamin is present in an amount of about 1 mg, said cyclic adenosine monophosphate is present in an amount of about 1 mg.

3. The method of claim 2 wherein said human is suffering from obesity.

4. The method of claim 2 wherein said human is seeking to reduce body weight by a moderate amount.

5. The method of claim 2 wherein said human is seeking to maintain a normal and healthy weight.

6. A method of claim 1 wherein the period of time I is about 1 week to about 3 months and the period of time II is about 1 week to about 3 months.

7. The method of claim 6 wherein the period of time I is about 21 days and the period of time II is about 7 days.

* * * * *